United States Patent [19]
Kent et al.

[11] Patent Number: 4,986,288
[45] Date of Patent: Jan. 22, 1991

[54] DENTAL FLOSS AND PICKS

[75] Inventors: Steven Kent, Heaton Norris; Sheila Downie, Stretford; Paul Slater, Marple, all of England

[73] Assignee: Colgate-Palmolive Company, Piscataway, N.J.

[21] Appl. No.: 172,034

[22] Filed: Mar. 23, 1988

[51] Int. Cl.$^5$ ............................................. A61C 15/00
[52] U.S. Cl. ........................................ 132/321; 424/50
[58] Field of Search ............... 132/321, 322, 323, 324, 132/326, 326, 327, 328, 329; 424/50

[56] References Cited

U.S. PATENT DOCUMENTS

| | | | |
|---|---|---|---|
| 973,842 | 10/1910 | Baird | 132/329 |
| 2,522,794 | 9/1950 | Medof | 132/325 |
| 2,700,636 | 1/1955 | Ashton | 424/54 |
| 3,838,702 | 10/1974 | Standish et al. | 132/321 |
| 3,929,988 | 12/1975 | Barth | 424/54 |
| 3,943,949 | 3/1976 | Ashton et al. | 132/321 |
| 4,098,879 | 7/1978 | Cousse et al. | 424/52 |
| 4,146,607 | 3/1979 | Ritchey | 424/54 |
| 4,175,326 | 11/1979 | Goodson | 433/80 |
| 4,220,552 | 9/1980 | Hitchcock | 424/52 |
| 4,235,875 | 11/1980 | Hernestam et al. | 424/54 |
| 4,307,077 | 12/1981 | Buck | 424/56 |
| 4,469,673 | 9/1984 | Iioka et al | 424/50 |
| 4,499,067 | 2/1985 | Silbering et al. | 424/52 |
| 4,556,561 | 12/1985 | Brown et al. | 424/52 |
| 4,585,482 | 4/1986 | Tice et al. | 424/149 |
| 4,585,649 | 4/1986 | Lynch | 424/49 |
| 4,597,960 | 7/1986 | Cohen | 424/147 |
| 4,645,662 | 2/1987 | Nakashima et al. | 424/50 |

FOREIGN PATENT DOCUMENTS

| | | | |
|---|---|---|---|
| 0052353 | 11/1982 | European Pat. Off. | |
| 0084440 | 6/1983 | European Pat. Off. | |
| 0109359 | 5/1984 | European Pat. Off. | |
| 0114113 | 7/1984 | European Pat. Off. | 132/321 |
| 0172671 | 2/1986 | European Pat. Off. | |
| 589016 | 6/1947 | United Kingdom . | |
| 1276031 | 6/1972 | United Kingdom . | |
| 1429121 | 3/1976 | United Kingdom . | |
| 2118069 | 10/1983 | United Kingdom . | |

Primary Examiner—John J. Wilson
Attorney, Agent, or Firm—Richard J. Ancel; Robert C. Sullivan; Murray M. Grill

[57] ABSTRACT

Dental floss and toothpicks (picks) incorporate one or more coagulants to retard and stop bleeding during flossing. In addition, or alternatively, the floss and picks incorporate tartar control, antiplaque and/or anti-bacterial agents.

3 Claims, 1 Drawing Sheet

DENTAL FLOSS AND PICKS

FIELD OF THE INVENTION

This invention relates to dental flosses and picks.

BACKGROUND

Dental flosses and picks have long been used to clean the teeth and the gum margin. In the past, certain medicinal ingredients have been incorporated within the picks and floss e.g., fluoride to protect the tooth enamel from acid attack. Bactericides have also been used to counter periodontal disease.

However, the use of picks and flossing—which are very important techniques recommended by dentists to prevent tooth and gum disease—often produces bleeding from the gums.

Thus, a primary object of this invention is to provide a dental cleaning device in the form of a toothpick (pick) or floss which incorporates one or more coagulants which inhibit such bleeding produced during the cleaning process, thereby to spare the user of the discomfort and distasteful presence of blood in the oral cavity.

Another important object of the invention is to incorporate in the picks and floss certain other agents which combat diseases in the oral cavity including anti-plaque agents, anti-bacterial agents and/or tartar control agents, preferably—although not necessarily—in conjunction with coagulants.

THE DRAWINGS

DETAILED DESCRIPTION

Figure 1:
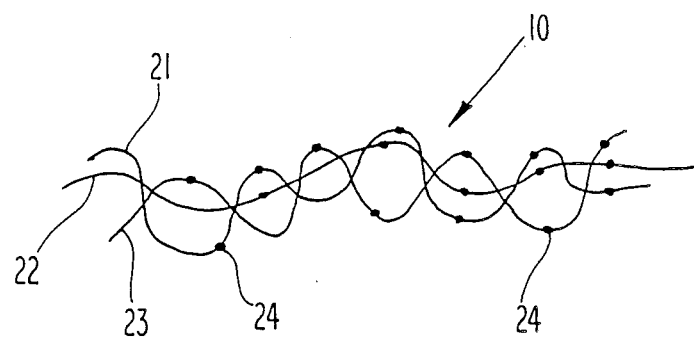
FIG. 1 illustrates in schematic form one embodiment of the improved dental floss of the present invention incorporating agents selected from the group comprising coagulant(s), antiplaque, anti-bacterial and tartar control agents.

By way of introduction, FIG. 1 is a schematic representation of a floss 10 of this invention which, for purposes of clarity, is shown as having only three filaments, 21, 22 and 23. In practice, a typical floss will comprise many more filaments which are typically intertwined. Adhered to the filaments are agents 24 selected from the group comprising coagulating agents, anti-plaque agents, tartar control agents and anti-bacterial agents. The agents 24 are shown as discrete particles, but in practice, the agents may well be incorporated throughout the filaments such as by coating or other techniques.

Figure 2:
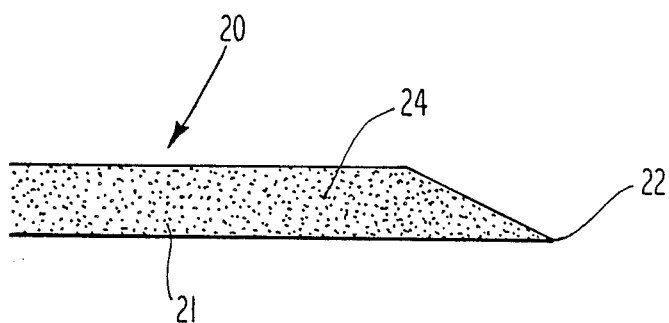
FIG. 2 illustrates a toothpick made in accordance with this invention on which there are the same agents as referred to in the description of FIG. 1.

FIG. 2 is a schematic view of a toothpick 20 of this invention having a main body 21 and a sharp pointed end 22. As in the case of floss 10, pick 20 incorporates agents 24 which are of the same type as agents 24 in FIG. 1.

FIG. 1 illustrates one type of floss 10 of this invention, namely, comprising a plurality of filaments of acceptable tensile strength. The filaments are illustrated as intertwined individual strands 21, 22 and 23. In actual practice, floss 10 normally would comprise a large number of filaments or strands. Suitable filaments may be in the form of a single strand or tape of any acceptable material such as nylon, polypropylene, polyester, silk, cotton, including cotton with a binding agent such as a modified nylon resin, vinyl acetate polymer, or Gantrez (polyvinyl methyl/ether/maleic anhydride copolymer) These materials usually are coated with a wax, which may be water soluble or insoluble (not shown). Acceptable waxes are, for example, microcrystalline hydrocarbon based waxes, silicone waxes and polyethylene glycol waxes, particularly polyethylene glycol having a molecular weight of at least about 1000 and preferably about 4000 to 6000.

The floss 10 preferably has incorporated within it one or more agents 24, which may be coagulants (or, "coagulating agents") to inhibit bleeding produced by flossing. Preferably, these "agents" are mixed in a wax coating and may include K vitamins (1–4), calcium ions in the form of a soluble (water) calcium salt and blood factors that initiate the coagulation cascade. It is possible to incorporate other coagulants from solution in finely dispersed form in a coating medium, such a wax (water soluble or otherwise). Alternatively, the coagulants may be solubilized in non-toxic solvents, e.g., ethanol, polyethylene terephthalate, ether, etc. Further, the coagulating agents may be incorporated when dry, in which case they are physically bound by the strands of the floss—such as by passing them through a fluidizeds bed.

In addition to the coagulants specified above, the following may be used in this invention, aminocuproic acid, tranexamic acid, adrenaline, alum, noradrenaline, iron salts and calcium alginate. Additional agents are described in Martindale (The Extra Pharmacopoeia), The Pharmaceutical Press, London. Ed. J. E. F. Reynolds.

It is important to get the coagulating agent(s) to the site of bleeding as quickly as possible. A preferred carrier in the floss 10 is a water soluble type of resin, such as PEG 6000 or 4000, together with floss binding agents, which are typically adhesives.

It is within the scope of this invention that the agent 24 in FIGS. 1 and 2 incorporate various other agents (or "actives" as they are referred to in the art) to attack other oral hygiene problems.

Thus, it may be desirable to incorporate the anti-plaque (anticalculus) agents of the type described in U.S. Pat. No. 4,627,977, commonly assigned, the disclosure of which patent is incorporated herein by reference.

Further, it may, under various circumstances, also be desirable to incorporate a tartar control agent. In this regard, a desirable formulation is pyrophosphate, preferably 3.3% pyrophosphate ion, NaF, preferably 0.2% and the polycarboxylate, Gantrez, preferably 1%. These percentages may vary, but, as noted in the '977 patent, the presence of fluoride ions tends to significantly inhibit the hydrolysis of the pyrophosphates by oral enzymes.

Other anti-tartar agents which may be incorporated in the floss 10 and pick 20 are zinc chloride, and pyrophosphate salts such as tetrasodium, sodium acid and tetrapotassium. The more soluble forms may be incorporated into water-soluble waxes, such as polyethylene glycol (PEG) types and stearates which are applied to floss 10.

With regard to the extent to which the tartar control agents actually release the agents, a test using a floss incorporating pyrophosphate with ten subjects has demonstrated that at least 12% of the agent was released in the worst case up to 83% in the best case. While this test may have a wide variation, the same probably reflects the different efficiencies with which the panellists flossed. In any event, it appears that a substantial amount of the aforesaid agent is released into the subgingival regions during flossing—and this is critically important to tartar control.

It appears that the optimum modality to ensure release of pyrophosphates incorporated in floss 10 is to utilize Gantrez (and its equivalents) as a binder for adhering that agent to floss 10 and pick 20 because it has been discovered that, of the three enzymes that cause the degradation of the pyrophosphate, NaF inhibits one and Gantrez inhibits the other two.

As noted above, it is also desirable in many cases to incorporate various antibiotics in the floss 10, and pick 20, either alone or in conjunction with the antiplaque, coagulant and/or tartar control agents described.

There is a fair amount of literature relating to the subject of the use of antibacterial agents in connection with the control of periodontal disease (PD). See, for example, the article by J. M. Goodson et al. entitled "Tetracycline-containing Fibers for Controlled Delivery to Periodontal Pockets", Journal Periodontal, Vol. 54 (10), pages 575-579, October 1983. However, while this and many other references acknowledge the general utility of antibiotics in controlling PD, they lack specific teachings relating to the mode of ensuring that such medicines actually reach the periodontal pockets where PD originates and grows.

Thus, the present invention, in teaching that the antibacterial agents (ABAs), such as tetracycline, can be most effectively employed by incorporating them in a floss 10 or a pick 20, is a significant advance in the art.

Although this invention covers the use of floss as a vehicle for the agents 24, there are certain situations where the use of toothpicks (picks) 20 as carriers for such medicaments offers significant advantages. Indeed, in certain circumstances, the dose can be more accurately established on a pick, e.g., in a range of from about 0.01 to 5 mg per pick or cm of floss of tetracycline, methacycline, oxytetracycline and their equivalents. It is a great advantage of this invention because the dose can be precisely fixed during manufacture and treatment can be administered in the home. In this embodiment of the invention, the carrying material for the antibiotic can be in the form of polyethylene glycol, e.g. of a MW of 1000-6000, or mixtures of that material and other carriers, preferably Gantrez.

In the above description, it has been generally set forth that the various agents described herein can be coated onto the floss or picks. However, it is also possible that the agents can be contained within microcapsules adhered to the floss or picks and which are deposited during flossing or inserting the pick into the sulcus or periodontal pocket. In this form of the invention, the agents can be released over a period of time.

If desired, a cooling agent such as menthol and analogs such as N-ether-p-methane-3-carboxamide may be incorporated in the coating or in the microcapsules to help the patient to detect where the treatment has been supplied.

As indicated, other agents may be applied or otherwise incorporated in the floss 10 and on pick 20 which promote oral hygiene, such as fluoride, chlorhexidine, hexachlorophene, soluble pyrophosphate salts with hydrolysis-inhibiting agent(s). Compounds that assist in wound healing such as allantoin, zinc sulphate and similar astringents may also be added to the floss 10 and pick 20.

The agent may be incorporated in the wax (not shown) used to coat floss 10 or pick 20 or may be embedded within the filament bundle of the floss 10. It may be desirable, for example, to immerse or coat the individual filaments 21, 22 and 23 with the agents prior to intertwining them into the bundle forms the floss 10. Thus, it should be understood that showing the agents 24 as discrete entities is for the purpose of illustration only. As indicated, they may be mixed thoroughly with the wax coating or applied to the outer surface of floss 10 and pick 20 or, at least in the case of floss 10, to the filament(s) forming the floss 10 in a manner that they extend throughout the floss structure.

A prime advantage of this invention may be summarized as follows: dental flosses and picks have long been used to remove particles and other debris by abrasive action. However, the use of these modualities—especially floss—has not been as high as desirable, in part due to the perception that flosses and picks do not provide substantial additional oral care effectiveness—and because they often cause bleeding.

The present invention, however, would encourage much greater use of the flosses and picks combined with the agents described herein because the user will be obtaining multiple benefits from not only abrasive action, but also from the action of the medications specified. In addition, flossing is especially effective in the sub-gingival areas and the use of anti-coagulants to reduce bleeding—which often occurs with present flosses—will eliminate the inhibition arising from bleeding and thus encourage more regular flossing.

We claim:

1. A dental floss made by the process comprising the following steps:
   applying a coating incorporating a dental agent on a first filament;
   applying a coating incorporating a dental agent on a second filament; and
   intertwining said first and second filaments after applying said coatings.

2. A process for making dental floss as defined in claim 1, wherein said dental agents are selected from the group consisting of antiplaque agents, vasoconstricting agents, coagulating agents, cooling agent, antibacterial agents, and tart control agents.

3. A process for making dental floss as defined in claim 1, wherein said coatings comprise wax.

* * * * *